(12) United States Patent
Tsujii

(10) Patent No.: US 6,766,044 B1
(45) Date of Patent: Jul. 20, 2004

(54) IMAGE PROCESSING APPARATUS AND METHOD, AND STORAGE MEDIUM

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 584 days.

(21) Appl. No.: 09/708,586

(22) Filed: Nov. 9, 2000

(30) Foreign Application Priority Data

Nov. 11, 1999 (JP) .......................................... 11-321207

(51) Int. Cl.[7] .......................... G06K 9/00; G01N 23/04
(52) U.S. Cl. ........................................ 382/132; 378/62
(58) Field of Search ............................... 382/132, 128, 382/159, 173, 199, 156; 250/584, 581, 587; 378/62, 901, 98.2, 98.7, 98.8

(56) References Cited

U.S. PATENT DOCUMENTS

| | | | |
|---|---|---|---|
| 4,258,264 A | | 3/1981 | Kotera et al. ................ 250/484 |
| 5,014,198 A | * | 5/1991 | Umemura ................... 382/232 |
| 5,651,042 A | * | 7/1997 | Dewaele ...................... 378/62 |
| 5,862,249 A | * | 1/1999 | Jang et al. ................... 382/132 |
| 6,018,562 A | * | 1/2000 | Willson ......................... 378/9 |
| 6,031,929 A | * | 2/2000 | Maitz et al. ................ 382/132 |
| 6,134,350 A | * | 10/2000 | Beck ........................... 382/240 |
| 6,212,291 B1 | * | 4/2001 | Wang et al. ................. 382/132 |
| 6,415,049 B1 | * | 7/2002 | Yanagita et al. ............ 382/132 |
| 6,421,468 B1 | * | 7/2002 | Ratnakar et al. ............ 382/254 |

FOREIGN PATENT DOCUMENTS

| | | |
|---|---|---|
| JP | 55-12429 | 1/1980 |
| JP | 56-11395 | 2/1981 |

OTHER PUBLICATIONS

Coifman, et al., "Entropy–Based Algorithms for Best Basis Selection," IEEE, 1992, pp. 713–718.*
Ramchandran et al., "Wavelets, Subband Coding, and Best Bases," IEEE, 1996, pp. 541–560.*

* cited by examiner

Primary Examiner—Daniel Mariam
Assistant Examiner—Shefali Patel
(74) Attorney, Agent, or Firm—Fitzpatrick, Cella, Harper & Scinto

(57) ABSTRACT

A discrete wavelet transformer computes the discrete wavelet transform of an input X-ray image, a quantizer quantizes coefficient values corresponding to a region of interest of the transformed coefficients as values relatively larger than coefficients corresponding to a non-region-of-interest, and an entropy encoder generates a code sequence by encoding the quantized coefficient values. The region of interest is extracted in such a manner that an irradiation region extraction unit detects an irradiation field region of X-rays of the input X-ray image, detects a through region by computing the histogram of pixel values of that irradiation field region, and removes the through region from the irradiation field region.

21 Claims, 14 Drawing Sheets

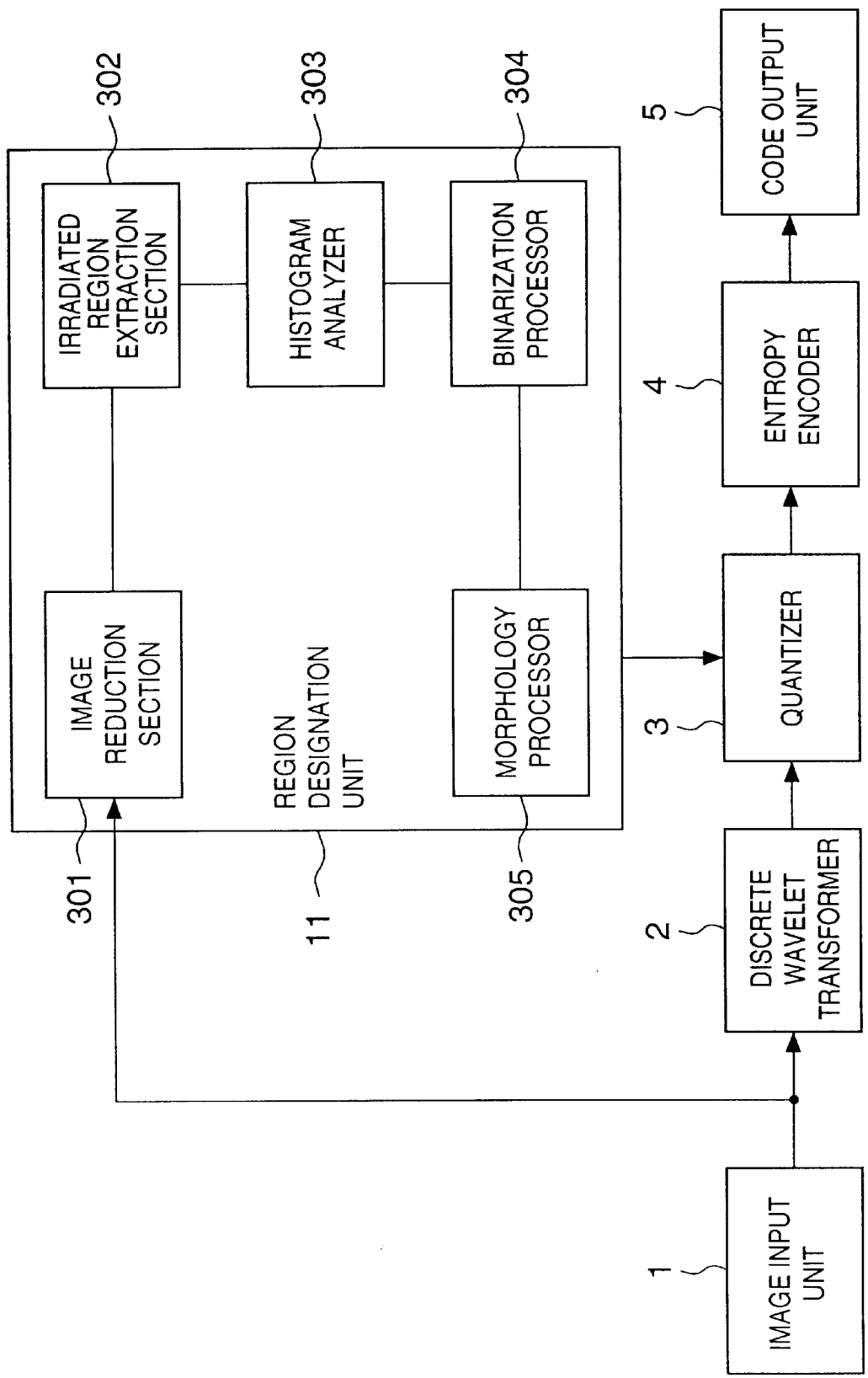

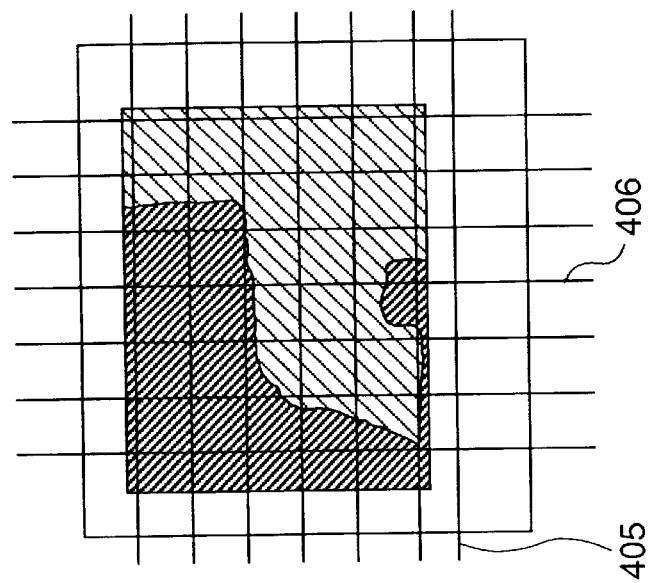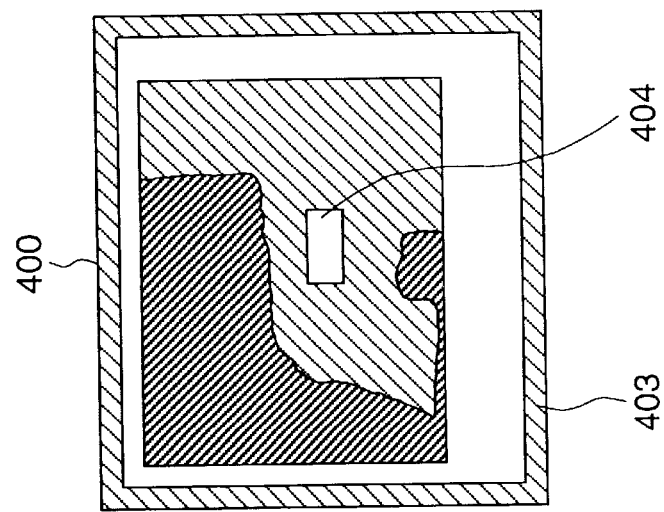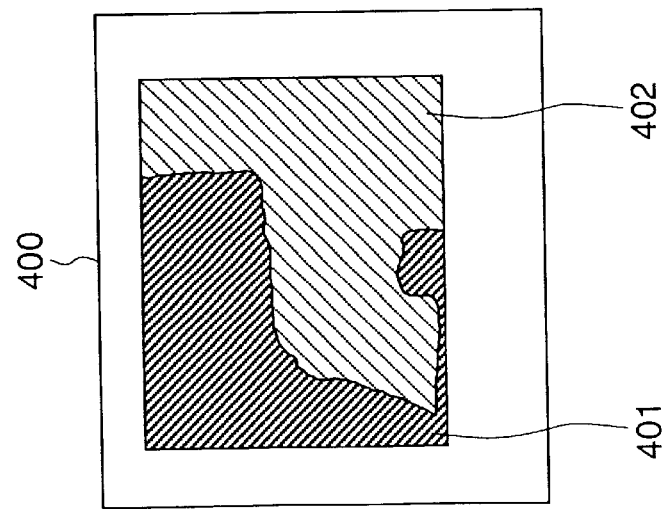

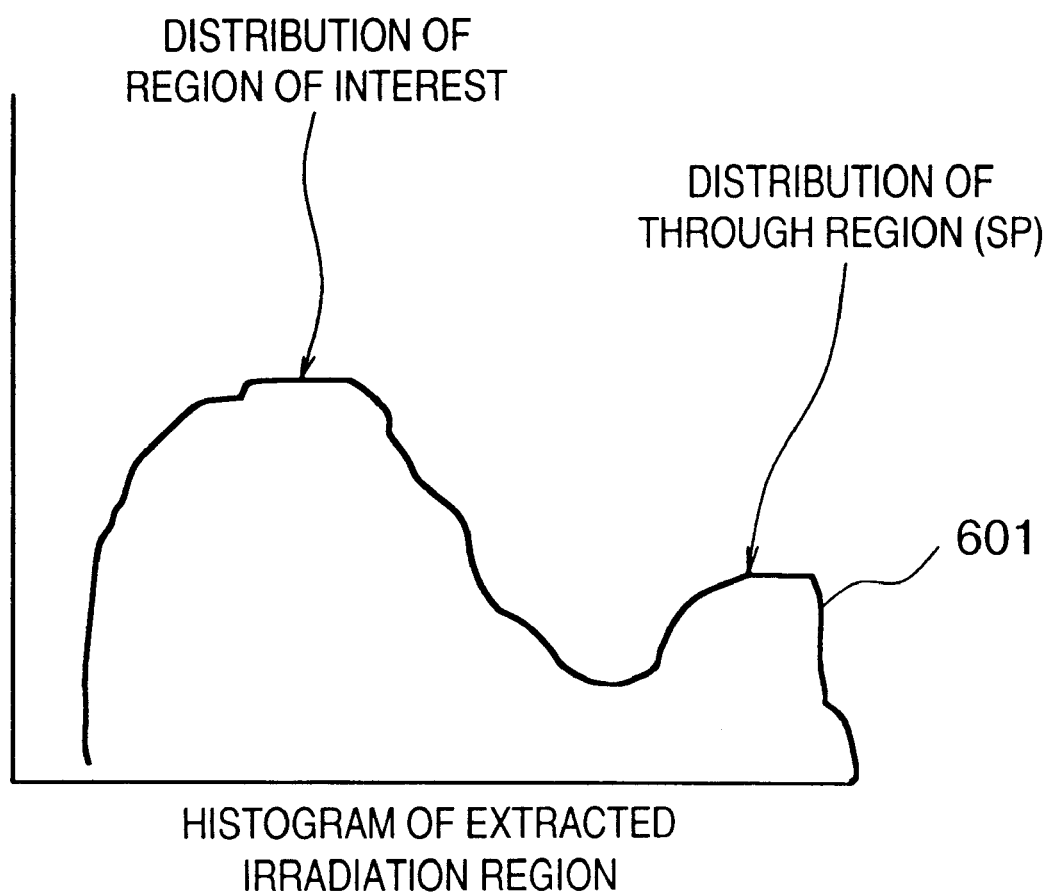

FIG. 8A

| MH | TH0 | BS0 | TH1 | BS1 | ------- | THn-1 | BSn-1 |

FIG. 8B

| IMAGE SIZE | TILE SIZE | NUMBER OF COMPONENTS | COMPONENT INFORMATION |

FIG. 8C

| TILE LENGTH | ENCODING PARAMETER | MASK INFORMATION | BIT SHIFT AMOUNT |

FIG. 8D

| LL | HL2 | LH2 | HH2 | HL1 | LH1 | HH1 |

| BIT PLANE S-1 | BIT PLANE S-2 | --------- | BIT PLANE 0 |

FIG. 9A

| MH | TH0 | BS0 | TH1 | BS1 | ... | THn-1 | BSn-1 |

FIG. 9B

| IMAGE SIZE | TILE SIZE | NUMBER OF COMPONENTS | COMPONENT INFORMATION |

FIG. 9C

| TILE LENGTH | ENCODING PARAMETER | MASK INFORMATION | BIT SHIFT AMOUNT |

FIG. 9D

| HL2 | LH2 | LL | ... | LL | HL2 | LH2 | HH2 | HL1 | LH1 | HH1 |

BIT PLANE S-1 | BIT PLANE S-2 | BIT PLANE 0

IMAGE PROCESSING APPARATUS AND METHOD, AND STORAGE MEDIUM

FIELD OF THE INVENTION

The present invention relates to an image processing apparatus and method for encoding an image signal, and a storage medium.

BACKGROUND OF THE INVENTION

When a given type of phosphor is irradiated with radiation (X-rays, α-rays, β-rays, γ-rays, electron beam, ultraviolet rays, or the like), it partially stores radiation energy. When that phosphor is then irradiated with excitation light, such as visible light or the like, it emits light by stimulation in accordance with the stored energy. The phosphor that exhibits such nature is called a storage phosphor (photostimulable phosphor). The present applicant has already proposed a radiation image information recording/reproduction system (Japanese Patent Laid-Open Nos. 55-12429, 56-11395, and the like). In this system, using such storage phosphor, radiation image information of an object to be sensed, such as a human body or the like, is temporarily recorded on a storage phosphor sheet, and the storage phosphor sheet is scanned while being irradiated with excitation light, such as a laser beam or the like, so as to emit light by stimulation. The emitted light is photoelectrically read so as to obtain an image signal, and a radiation image of the object is output as a visible image to a recording medium, such as a photosensitive material, or to a display device, such as a CRT or the like, on the basis of the image signal.

Also, an apparatus which senses an X-ray image of an object, by light emitted by stimulation using a semiconductor sensor in the same manner as in the above system, has been developed in recent years. Such apparatus has a practical merit, i.e., it can record an image over a much broader radiation exposure range than a radiation photographic system using conventional silver halide photographs. That is, X-rays over a very broad range are read by photoelectric conversion means so as to be converted into an electrical signal, and a visible image based on a radiation image is output to a recording medium, such as a photosensitive material, or to a display device, such as a CRT or the like, using the electrical signal, thus obtaining a radiation image which is free from any variations of the dose of radiation.

Since such X-ray image contains a very large amount of information, storage or transmission of that image information requires a huge information volume. For this reason, storage and transmission of such image information use high-efficiency coding that reduces the data size by removing redundancy of an image or changing the contents of an image to a degree at which deterioration of image quality is not visually recognizable.

For example, JPEG recommended by ISO and ITU-T as an international standard coding scheme of still image uses DPCM for reversible compression, and discrete cosine transformation (DCT) for irreversible compression. A detailed description of JPEG will be omitted since they are described in ITU-T Recommendation T.81 | ISO/IEC 10918-1 and the like.

In recent years, many studies about compression methods using discrete wavelet transformation (DWT) have been made. One feature of the compression method using DWT is that it is free from any blocking artifact which is observed in DCT.

On the other hand, as for compression of an X-ray image, the following means for efficiently improving the compression ratio may be used. That is, a region of interest (important region) is set, a low compression ratio is set in that region of interest to minimize deterioration of image quality, and the image of the region of interest is preferentially used compared to those of other regions. However, it is not always easy to select a position of an image where the region of interest is set, since it may require some knowledge concerning medical diagnosis.

SUMMARY OF THE INVENTION

The present invention has been made in consideration of the above prior art, and has as its object to provide an image processing method and apparatus which can automatically encode a region of interest of an X-ray image, and a storage medium.

It is another object of the present invention to provide an image processing method and apparatus which compress and encode a region of interest of an X-ray image so as to be able to be decoded earlier than other regions, thereby encoding the region of interest at a low compression ratio with high image quality, and a storage medium.

It is still another object of the present invention to provide an image processing method and apparatus which can decode a region of interest of an X-ray image with higher image quality.

In order to attain the above described objects, an image processing apparatus of the present invention for encoding an X-ray image, comprising:

irradiation field detection means for detecting an X-ray irradiation field region of an input X-ray image; through region detection means for detecting a through region in the irradiation field region detected by said irradiation field detection means; region of interest extraction means for extracting a region of interest in the irradiation field region on the basis of the through region detected by said through region detection means; transformation means for transforming the X-ray image using a discrete wavelet transformation; and encoding means for encoding coefficient values corresponding to the region of interest of coefficients obtained by said transformation means after shifting up the coefficient values with respect to coefficients corresponding to the non-region-of-interest.

In order to attain the above described objects, an image processing method of the present invention for encoding an X-ray image, comprising:

an irradiation field detection step of detecting an X-ray irradiation field region of an input X-ray image; a through region detection step of detecting a through region in the X-ray irradiation field region; a region of interest extracting step of extracting a region of interest in the irradiation field region on the basis of the through region; a transformation step of transforming the X-ray image by using a discrete wavelet transformation and obtaining coefficient values; and an encoding step of encoding the coefficient values after shifting up the coefficient values with respect to coefficients corresponding to the non-region-of-interest.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

FIG. 1 is a block diagram showing the arrangement of an image encoding apparatus according to an embodiment of the present invention;

FIGS. 4A to 4C are views for explaining an example of the region of interest extracted from the irradiated region of an X-ray image in the embodiment of the present invention;

FIG. 6 is a view for explaining an example of the region of interest extracted from the irradiated region of an X-ray image in the embodiment of the present invention;

FIGS. 8A to 8D are schematic views showing the format of a code sequence to be generated and output by spatial scalability;

FIGS. 9A to 9D are schematic views for explaining the format of a code sequence to be generated and output in case of SNR scalability;

DETAILED DESCRIPTION OF THE PREFERRED EMBODIMENTS

Figure 2A:
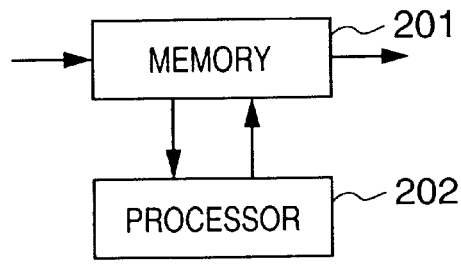
FIGS. 2A to 2C are views for explaining the arrangement of a wavelet transformer according to the embodiment of the present invention, and subbands obtained by transformation.

A preferred embodiment of the present invention will be described in detail hereinafter with reference to the accompanying drawings.

As a feature of this embodiment, an input image is analyzed to extract a region irradiated with X-rays, an X-ray through region is further extracted from the extracted irradiated region, a portion obtained by excluding the X-ray through region from the irradiated region is determined as a region of interest (designated region), and image data corresponding to the region of interest is encoded after level shifts up, thus preferentially encoding the region of interest. When a code sequence encoded in this way is decoded, the quantization indices of that region of interest are decoded earlier than other portions. For this reason, when, for example, a decoding process is interrupted, an image in which the region of interest is, in the present moment, restored to have higher quality than other regions is obtained, because the image data of the region of interest has been encoded after shifting up of bits of the quantization indices and the encoded image data is output from a higher bit order.

An embodiment of the present invention will be described in detail below.

FIG. 1 is a block diagram showing the arrangement of an image encoding apparatus according to an embodiment of the present invention.

Referring to FIG. 1, reference numeral 1 denotes an image input unit for inputting image data. The image input unit 1 may comprise an image sensing device such as a scanner, digital camera, or the like for scanning a document image, an interface unit having an interface function with a communication line, or the like. Reference numeral 2 denotes a discrete wavelet transformer for computing the two-dimensional discrete wavelet transform of the input image. Reference numeral 3 denotes a quantizer for quantizing coefficients obtained by discrete wavelet transformation of the discrete wavelet transformer 2. Reference numeral 4 denotes an entropy encoder for entropy-encoding the coefficients quantized by the quantizer 3. Reference numeral 5 denotes a code output unit for outputting codes encoded by the entropy encoder 4. Reference numeral 11 denotes a region designation unit for designating the region of interest of an image input from the image input unit 1.

Note that the apparatus according to the first embodiment is not limited to a dedicated apparatus shown in FIG. 1, and the present invention can be applied to, e.g., a case wherein a versatile PC or workstation loads a program to implement the aforementioned functions.

In the above arrangement, the image input unit 1 inputs pixel signals that form an image to be encoded in the raster scan order, and its output is input to the discrete wavelet transformer 2. In the following description, an image signal input from the image input unit 1 is expressed by a monochrome multi-valued image. However, upon encoding a plurality of color components of a color image or the like, each of R, G, and B color components or luminance and chromaticity components can be compressed as the monochrome component.

The discrete wavelet transformer 2 executes a two-dimensional wavelet transformation process for the input image signal, and computes and outputs transform coefficients.

Figure 2B:
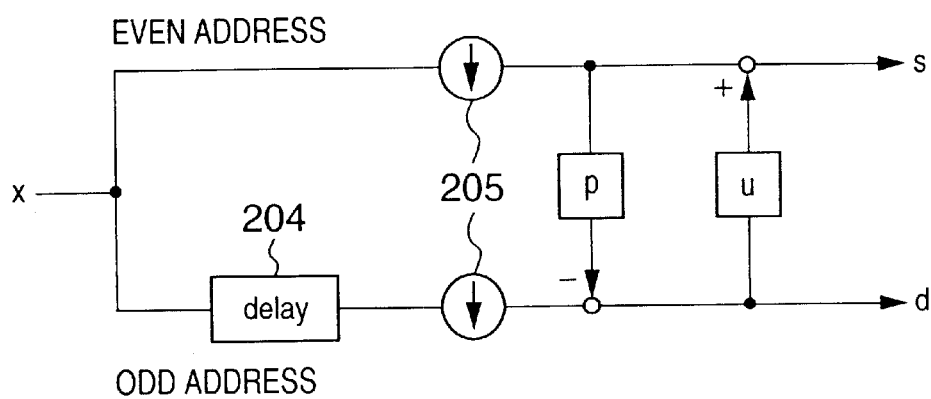
Figure 2C:
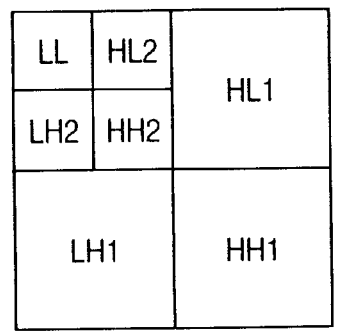

FIGS. 2A to 2C are views for explaining the basic arrangement and operation of the discrete wavelet transformer 2 according to this embodiment.

An image signal input from the image input unit 1 is stored in a memory 201, is sequentially read out by a processor 202 to undergo the discrete wavelet transformation process, and is stored in the memory 201 again.

FIG. 2B shows the arrangement of the process in the processor 202. Referring to FIG. 2B, the input image signal is separated into odd and even address signals by a combination of a delay element 204 and down samplers 205, and these signals undergo filter processes of two filters p and u. In FIG. 2B, s and d represent low- and high-pass coefficients upon breaking up a linear image signal to one level, and are respectively computed by:

$$d(n)=x(2n+1)-\mathrm{floor}((x(2n)+x(2n+2))/2) \quad (1)$$

$$s(n)=x(2n)+\mathrm{floor}((d(n-1)+d(n))/4) \quad (2)$$

where x(n) is an image signal to be transformed, and floor(x) is a function of outputting a maximum integer smaller than x.

With this process, the linear discrete wavelet transformation process is done for an image signal from the image input unit 1. Since two-dimensional discrete wavelet transformation is implemented by sequentially executing linear discrete wavelet transformation in the horizontal and vertical directions of an image and its details are known to those who are skilled in the art, a description thereof will be omitted.

FIG. 2C shows an example of the format of two levels of transformation coefficient groups obtained by the two-dimensional discrete wavelet transformation process. An image signal is broken up into coefficient sequences HH1, HL1, LH1, HL2 ..., LL in different frequency bands. Note that these coefficient sequences will be referred to as subbands hereinafter. The coefficients of the individual subbands are output to the quantizer 3.

The region designation unit 11 determines an ROI (Region Of Interest) to be decoded to have higher image quality than surrounding (other) portions in an image to be encoded, and generates mask information indicating coefficients that belong to the ROI upon computing the discrete wavelet transforms of the image to be encoded. Note that details of the region designation unit 11 will be described later.

Figure 3A:
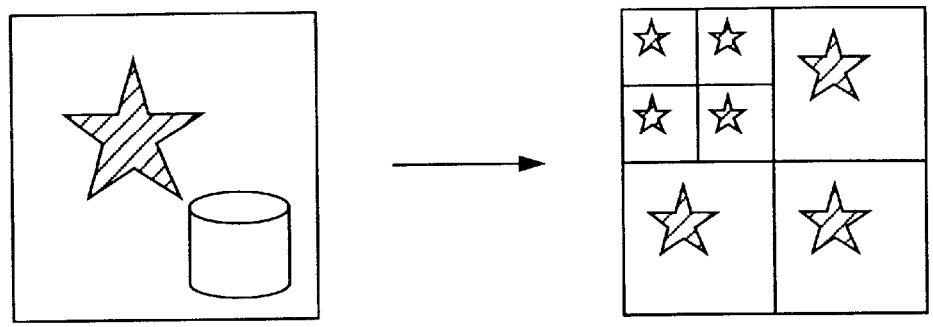
FIGS. 3A to 3C are views for explaining transformation of the region of interest (designated region) in an image and bit shifts of image data in that region.

FIG. 3A is a view for explaining the principle upon generating mask information.

Assuming that a star-shaped region is designated as the ROI (to be referred to as a designated region hereinafter), as shown in the left image in FIG. 3A, the region designation unit 11 computes portions to be included in respective subbands upon computing the discrete wavelet transforms of the image including this designated region. The region indicated by this mask information corresponds to a range including transform coefficients of the surrounding region required for reconstructing an image signal on the boundary of the designated region.

The right image in FIG. 3A shows an example of the mask information computed in this way. In this example, mask information upon discrete wavelet transformation of the left image to two levels in FIG. 3A is computed, as shown in FIG. 3A. In FIG. 3A, a star-shaped portion corresponds to the designated region, bits of the mask information in this designated region are set at "1", and other bits of the mask information are set at "0". Since the entire mask information has the same format as transform coefficients of two-dimensional discrete wavelet transformation, whether or not a coefficient at a given position belongs to the designated region can be identified by checking the corresponding bit in the mask information. The mask information generated in this manner is output to the quantizer 3.

Furthermore, the region designation unit 11 receives parameters for designating image quality of that designated region from an input system (not shown). These parameters may be either numerical values that express a compression ratio to be assigned to the designated region or those indicating image quality. In this case, the compression ratio to be assigned can be determined by portion information of the sensed image (captured image). The sensed portion information indicates the sensed portion and captured view direction such as a front chest image, side head image, or the like in case of X-ray images. Such information may be input by the operator using a control panel (not shown) of the image input unit 1 or may be transferred from a radiation information system (not shown) prior to image sensing (photographing). In general, since chest image contains soft tissue, it is required not to set so high compression ratio. On the other hand, a bone image like a head image hardly deteriorates considerably even when a high compression ratio is set. The region designation unit 11 computes a bit shift amount B for coefficients in the designated region, and outputs it to the quantizer 3 together with the mask information.

The arrangement of the region designation unit 11 that automatically determines the designated region (ROI) will be explained in detail below.

As shown in FIG. 1, the region designation unit 11 comprises an image reduction section 301, an irradiated region extraction section 302, a histogram analyzer 303, a binarization processor 304, and a morphology processor 305. The image reduction section 301 outputs a reduced-scale image of about (336×336) pixels with respect to an input image of (2,688×2,688) pixels. In order to shorten the arithmetic operation time of the subsequent processes, the pixel value of an input image may be expressed by 12 bits, and the input image may be converted into 8-bit reduced-scale image data by deleting lower 4 bits of the 12-bit pixel data.

The irradiated region extraction section 302 extracts the distribution of X-ray incident regions of the entire input image. The X-ray incident regions may be distributed on the entire input image but only a given portion may be irradiated with X-rays (such case corresponds to the "presence of an irradiation field stop").

The process for discriminating the presence/absence of an irradiation field stop will be explained first with reference to FIGS. 4A–4C, 5A–5C, and 6.

FIG. 4A shows an example of an input image. If this input image region 400 has an irradiation field stop, and includes an X-ray non-irradiated portion, such non-irradiated portion may be present on a peripheral region of the image. For this reason, the average pixel value of the peripheral region of the input image region 400 is compared with that of the central portion of the input image. If the average pixel value of the peripheral region is around 5% or more smaller than that of the central portion, it can be empirically determined that the image has the irradiation field stop. In FIG. 4A, reference numeral 401 denotes an X-ray irradiated region; and 402, an ROI.

FIG. 4B shows an example of a peripheral region 403 and central region 404 in the input image region 400.

The process executed when the irradiation field stop is present will be explained below. Some profiles are extracted respectively in the vertical and horizontal directions of the input image region 400. Two peak points are extracted from the second derivatives of these extracted profiles. The coordinates of the peak values of the second derivatives of a plurality of profiles are computed to obtain an average line segment, thus obtaining a line segment which indicates the irradiation field region.

FIG. 4C exemplifies the positions of horizontal and vertical profiles 405 and 406 as examples of profile positions.

Figure 5A:
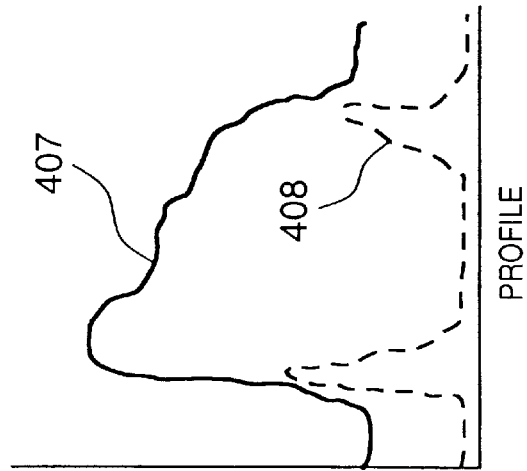
FIGS. 5A to 5C are views for explaining an example of the region of interest extracted from the irradiated region of an X-ray image in the embodiment of the present invention.
Figure 5B:
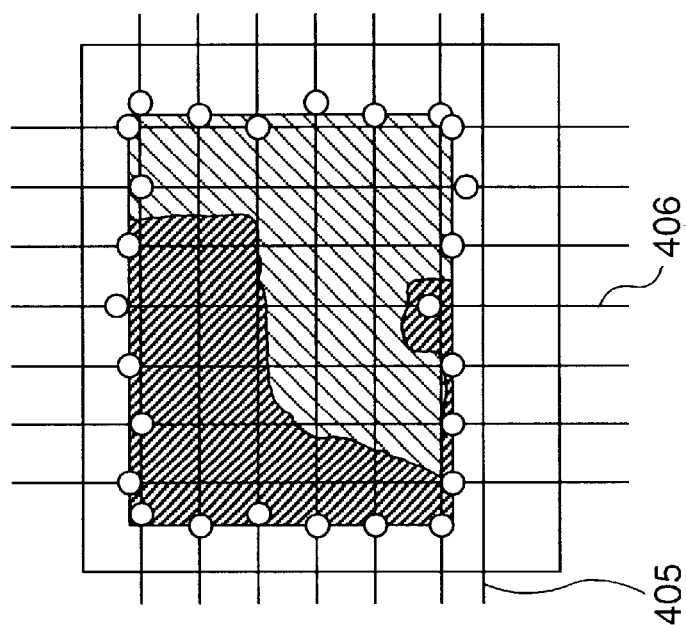
Figure 5C:
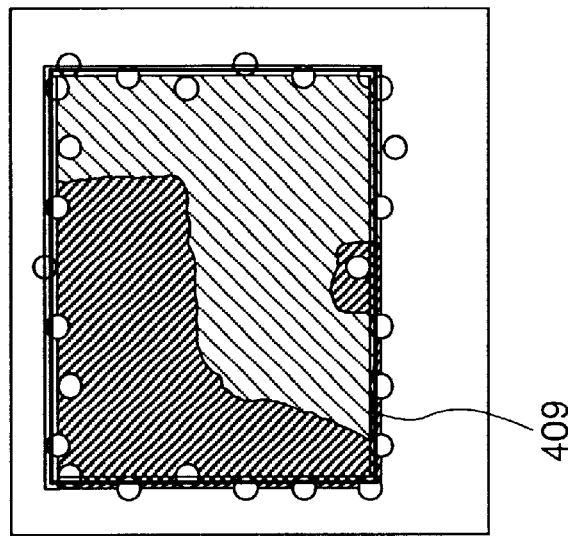

FIG. 5A shows an example of peak detection using the second derivatives of profiles. In FIG. 5A, a solid curve 407 indicates a profile detection result, and a dotted curve 408 indicates a second derivative result. FIG. 5B shows the detection positions of the horizontal and vertical profiles 405 and 406 by circular marks. Also, FIG. 5C shows a finally extracted irradiation field region 409, which corresponds to the X-ray irradiated region 401 in FIG. 4A. The process in the irradiated region extraction section 302 has been explained.

The histogram analyzer 303 computes the frequencies of occurrence of pixel values for the irradiation field region 409 extracted as the irradiated region by the irradiated region extraction section 302. Note that pixel values increase as the amount of irradiated X-ray increases. It is checked, based on the histogram analysis result, if an X-ray through region is present. When an X-ray through region is present, since two peaks are present, the presence/absence of a through region can be determined based on them.

In general, upon sensing an image of an abdomen, chest, or the like that has an irradiation field stop but not the X-ray through region, only one peak appears, despite the presence of bones and soft tissue. In the method of detecting the number of peaks, a histogram, which is assumed to be a waveform, is filtered using a low-pass filter, and then undergoes a second derivative process. When the second derivative process value exceeds a threshold value which is set empirically, the presence of a peak is determined. In very rare occasions, no peak is detected or three or more peaks are detected. When no peak is detected, the absence of an X-ray through region is determined; when three or more peaks are detected, two out of three or more peaks are selected in descending order, and a peak having a larger pixel value is determined to be an X-ray through region.

FIG. 6 shows the histogram in the irradiation field region 409, and a peak 601 of the detected through region. When the presence of an X-ray through region is determined, binarization is done by the binarization processor 304 using a peak value SP of the X-ray through region. A region having pixel values equal to or larger than the peak value SP is determined to be an X-ray through region, and a region having pixel values smaller than the peak value SP is determined to be a region to be sensed.

Since the binarization processor 304 is likely to leave isolated points or an X-ray through region, the morphology processor 305 executes a filter process. Erosion for removing the isolated points and a remaining X-ray through region is done for around three to five pixels. After that, a labeling process is done to limit the region to one continuous region. In this stated, since a continuous region may have a hole, the hole is closed by a closing process. That output result corresponds to the ROI obtained by removing the X-ray through region from the irradiation field region 409 shown in FIG. 5C. In the following description, assume that the ROI has a star shape shown in FIG. 3A for the sake of convenience.

The quantizer 3 quantizes the input coefficients by a predetermined quantization step, and outputs indices corresponding to the quantized values. In this case, quantization is described by:

$$q=\text{sign}(c)\text{floor}(abs(c)/\Delta) \quad (3)$$

$$\text{sign}(c)=1; \quad c \geq 0 \quad (4)$$

$$\text{sign}(c)=-1; \quad c<0 \quad (5)$$

where c is a coefficient to be quantized. In this embodiment, the value $\Delta$ includes "1". However, when $\Delta=1$, no quantization is done in practice.

The quantizer 3 changes the quantization index on the basis of the mask and shift amount B input from the region designation unit 11 by:

$$q'=q \times 2^B; \quad m=1 \quad (6)$$

$$q'=q; \quad m=0 \quad (7)$$

where m is the mask value at the position of the quantization index of interest. With the aforementioned process, only quantization indices that belong to the spatial region designated by the region designation unit 11 are shifted to the MSB side by B bits.

Figure 3B:
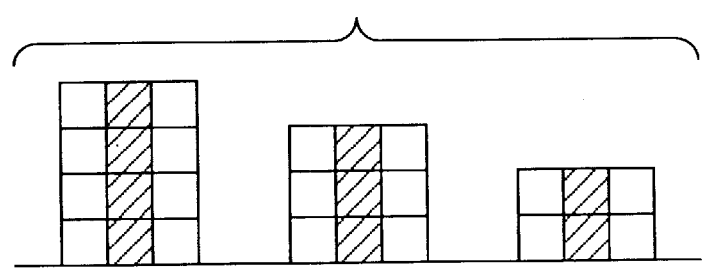
Figure 3C:
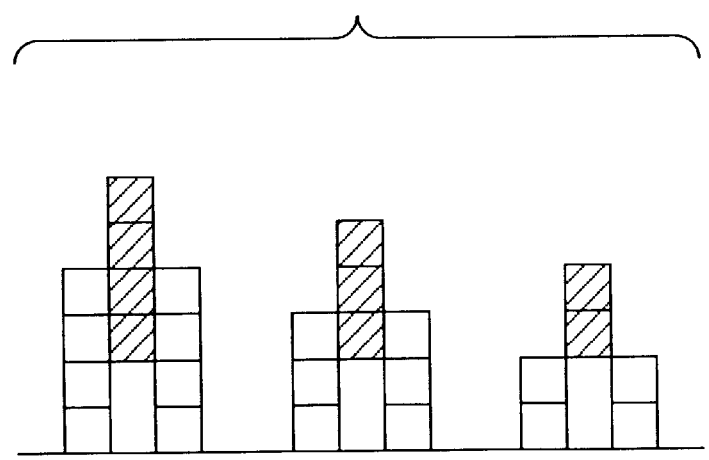

FIGS. 3B and 3C show changes in quantization index by a bit-shift-up process. In FIG. 3B, when three quantization indices are respectively present in three subbands, and the mask value="1" and the shift value B="2" in the hatched quantization indices, the quantization indices after bit shifts are as shown in FIG. 3C.

The quantization indices changed in this manner are output to the entropy encoder 4.

The entropy encoder 4 segments the quantization indices input from the quantizer 3 into bit planes, executes binary arithmetic coding in units of bit planes, and outputs a code stream.

Figure 7:
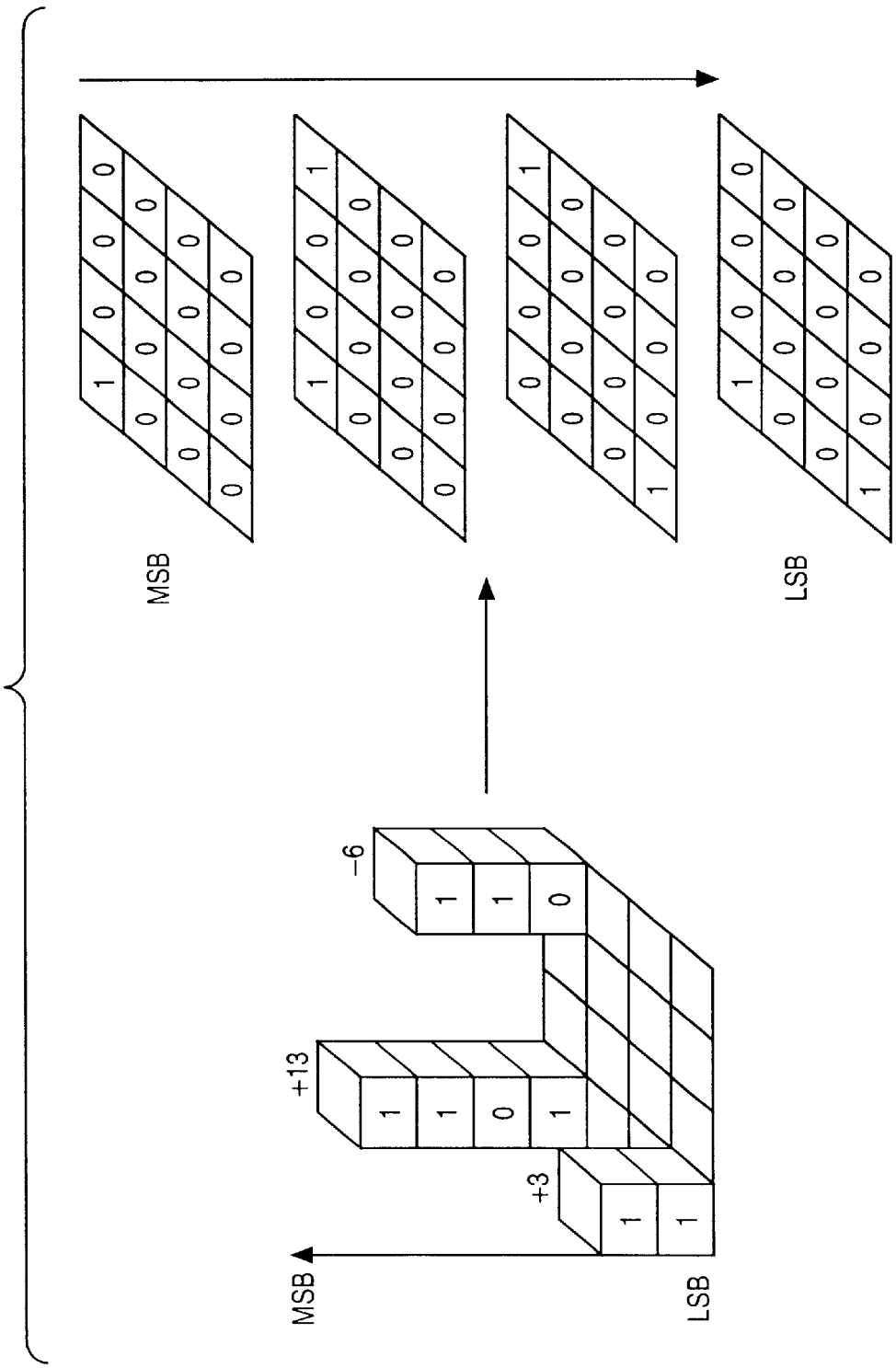
FIG. 7 is a view for explaining the operation of an entropy encoder according to the first embodiment.

FIG. 7 is a view for explaining the operation of the entropy encoder 4. In this example, a 4×4 subband region includes three nonzero indices, which respectively have values "+13", "−6", and "+3". The entropy encoder 4 scans this region to obtain a maximum value M ("13" in this example), and computes the number S of bits required for expressing the maximum quantization index by:

$$S=\text{ceil}(\log_2(abs(M))) \quad (8)$$

where ceil(x) is the smallest one of integers equal to or larger than x.

In FIG. 7, since the maximum coefficient value is "13", the value of S is "4", and 16 quantization indices in the sequence are processed in units of four bit planes, as indicated by the right side in FIG. 7. The entropy encoder 4 makes binary arithmetic coding of bits of the most significant bit plane (indicated by MSB in FIG. 7) and outputs the coding result as a bitstream. Then, the encoder 4 lowers the bit plane by one level, and encodes and outputs bits of each bit plane to the code output unit 5 until the bit plane of interest reaches the least significant bit plane (indicated by LSB in FIG. 7). At this time, a code of each quantization index is entropy-encoded immediately after the first nonzero bit is detected upon scanning the bit plane.

Entropy coding includes two schemes, i.e., a spatial scalable scheme and SNR scalable scheme. In the spatial scalable scheme, image quality can be improved in turn from an image with a lower resolution to an image with a higher resolution upon transferring and rasterizing information. In the SNR scalable scheme, the spatial resolution remains the same, and an image can be displayed while improving the image quality.

The spatial scalable scheme will be explained first.

FIGS. 8A to 8D show the format of a code sequence to be generated and output in this fashion.

FIG. 8A shows the overall format of a code sequence, in which MH is a main header; THi (i=0 to n−1), a tile header; and BSi (i=0 to n−1), a bitstream. The main header MH is comprised of the size (the numbers of pixels in the horizontal and vertical directions) of an image to be encoded, a size upon breaking up the image into tiles as a plurality of rectangular regions, the number of components indicating the number of color components, the size of each component, and component information indicating bit precision, as shown in FIG. 8B. In this embodiment, since an image is not broken up into tiles, the tile size is equal to the image size, and when the image to be encoded is a monochrome multi-valued image, the number of components is "1".

FIG. 8C shows the format of the tile header TH. The tile header TH consists of a tile length including the bitstream length and header length of the tile of interest, an encoding parameter for the tile of interest, mask information indicating the designated region, and the bit shift amount (see FIG. 3C) for coefficients that belong to the designated region. The encoding parameter includes a discrete wavelet transform level, filter type, and the like.

When the aforementioned bit shift up amount B is equal to the number of bits used to express each source quantization index, i.e., when bit shift up which does not include both an ROI portion and non-ROI portion on each bit plane is executed, the decoding apparatus can determine the ROI portion and can decode normally even when the encoded data does not include any mask information.

FIG. 8D shows the format of a bitstream in this embodiment. In FIG. 8D, the bitstream is formed in units of subbands, which are arranged in turn from a subband (LL) having a low resolution in ascending order of resolution. Furthermore, in each subband, codes are set in units of bit planes, i.e., in the order from an upper bit plane (bit plane (S-1)) to a lower bit plane (bit plane 0).

With this code sequence, hierarchical decoding shown in FIGS. 13A and 13B (to be described later) can be done.

The SNR scalable scheme will be explained below.

FIGS. 9A to 9D are schematic views for explaining the format of a code sequence to be generated and output in the SNR scalable scheme.

FIG. 9A shows the overall format of a code sequence, in which MH is a main header; THi (i=0 to n−1), a tile header; and BSi (i=0 to n−1), a bitstream. The main header MH is comprised of the size (the numbers of pixels in the horizontal and vertical directions) of an image to be encoded, a tile size upon breaking up the image into tiles as a plurality of rectangular regions, the number of components indicating the number of color components, the size of each component, and component information indicating bit precision, as shown in FIG. 9B. In this embodiment, since an image is not broken up into tiles, the tile size is equal to the image size, and when the image to be encoded is a monochrome multi-valued image, the number of components is "1".

FIG. 9C shows the format of the tile header TH.

The tile header TH consists of a tile length including the bitstream length and header length of the tile of interest, an encoding parameter for the tile of interest, mask information indicating the designated region, and the bit shift amount (see FIG. 3C) for coefficients that belong to the designated region. The encoding parameter includes a discrete wavelet transform level, filter type, and the like.

FIG. 9D shows the format of a bitstream in this embodiment. The bitstream is formed in units of bit planes, which are set in the order from an upper bit plane (bit plane (S-1)) to a lower bit plane (bit plane (0)). In the bit planes, the encoding results of the bit planes of a given quantization index in each subband are sequentially set in units of subbands. In FIG. 9D, S indicates the number of bits required for expressing the maximum quantization index. The code sequence generated in this manner is output to the code output unit 5.

With this code sequence, hierarchical decoding shown in FIGS. 14A and 14B (to be described later) can be done.

In this embodiment, the compression ratio of the entire image to be encoded can be controlled by changing the quantization step $\Delta$.

As another method, in this embodiment, lower bits of a bit plane to be encoded by the entropy encoder 4 can be limited (discarded) in correspondence with a required compression ratio. In this case, not all bit planes are not encoded, but bit planes from the most significant bit plane to a bit plane corresponding in number to the required compression ratio are encoded and are included in a final code sequence.

In this manner, by adopting a function of limiting lower bit planes, only bits corresponding to the designated region are included in large quantity in the code sequence, as shown in FIGS. 3A to 3C. That is, since the designated region is compressed at a low compression ratio, it can be encoded as a high-quality image.

A method of decoding a bitstream encoded by the aforementioned image encoding apparatus will be explained below.

Figure 10:
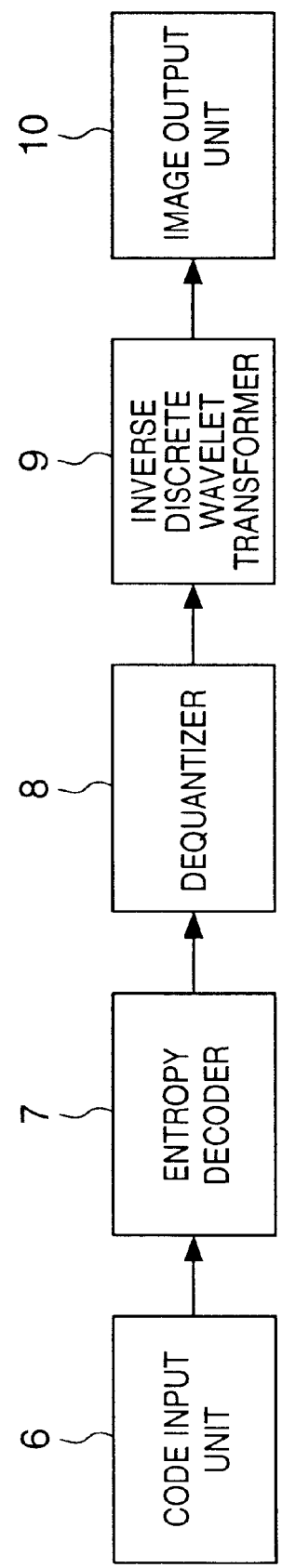
FIG. 10 is a block diagram showing the arrangement of an image decoding apparatus according to the embodiment of the present invention.

FIG. 10 is a block diagram showing the arrangement of an image decoding apparatus according to this embodiment. Reference numeral 6 denotes a code input unit; 7, an entropy decoder; 8, a dequantizer (inverse-quantizer); 9, an inverse discrete wavelet transformer; and 10, an image output unit. Note that the image processing apparatus of this embodiment may comprise at least one or both of the encoding apparatus shown in FIG. 1 and the decoding apparatus shown in FIG. 10.

The code input unit 6 receives a code sequence encoded by, e.g., the aforementioned encoding apparatus (FIG. 1), analyzes the header included in that sequence to extract parameters required for the subsequent processes, and controls the flow of processes if necessary or outputs required parameters to the subsequent processing units. The bitstreams included in the input code sequence are output to the entropy decoder 7.

Figure 11:
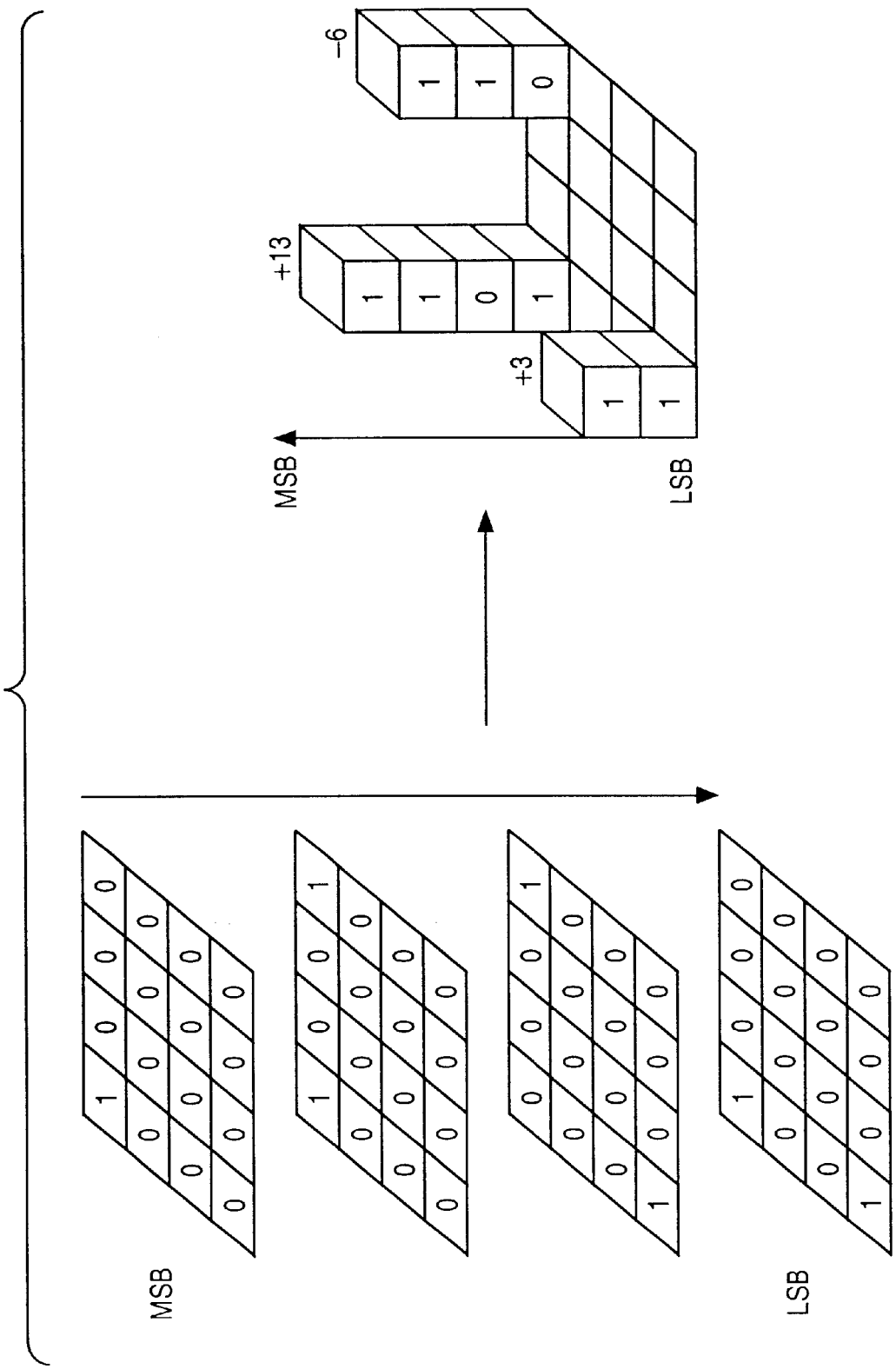
FIG. 11 is a view for explaining the bit planes and the decoding order in units of bit planes of an entropy decoder in the embodiment of the present invention.

The entropy decoder 7 decodes and outputs the bitstreams in units of bit planes. FIG. 11 shows the decoding sequence at that time. FIG. 11 illustrates transformation opposite to FIG. 7.

The left side in FIG. 11 illustrates the flow for sequentially decoding one subband region to be decoded in units of bit planes to finally restore a quantization index, and bit planes are decoded in the order of an arrow. The restored quantization indices are output to the dequantizer 8.

The dequantizer 8 restores discrete wavelet transform coefficients from the input and decoded quantization indices by:

$$c' = \Delta \times q/2^U; \; q \neq 0 \tag{9}$$

$$c' = 0; \; q = 0 \tag{10}$$

$$U = B; \; m = 1 \tag{11}$$

$$U = 0; \; m = 0 \tag{12}$$

where q is the quantization index, and $\Delta$ is the quantization step, which is the same value used upon encoding. B is the bit shift amount read out from the tile header, and m is the mask value at the position of the quantization index of interest. c' is the restored transform coefficient, which is obtained by restoring the coefficient s or d in the encoding. This transform coefficient c' is supplied to the inverse discrete wavelet transformer 9.

Figure 12A:
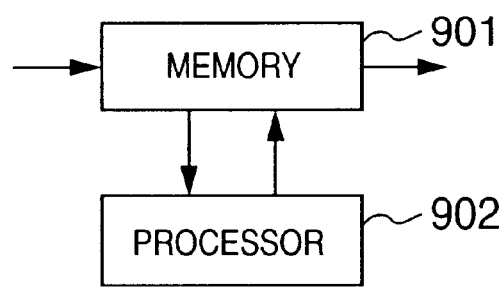
FIGS. 12A and 12B are block diagrams showing the arrangement of a wavelet decoder according to the embodiment of the present invention.
Figure 12B:
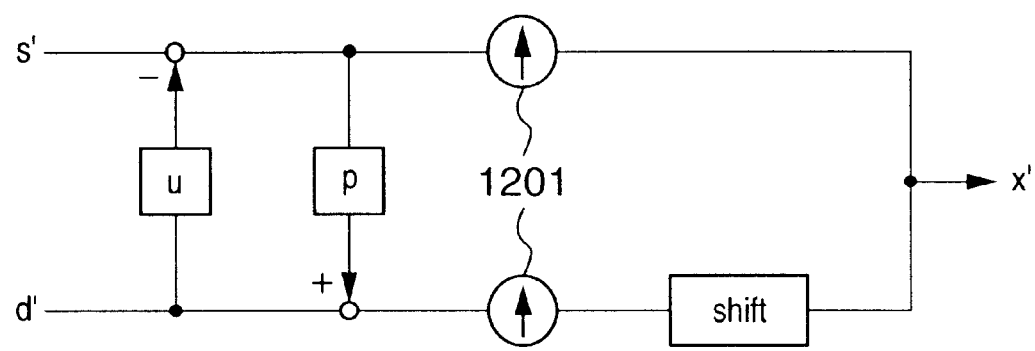

FIGS. 12A and 12B are block diagrams showing the arrangement and process of the inverse wavelet transformer 9 according to the embodiment of the present invention.

Referring to FIG. 12A, the input transform coefficients are stored in a memory 901. A processor 902 executes a linear inverse discrete wavelet transform process while sequentially reading out the transform coefficients from the memory 901, thus implementing a two-dimensional inverse discrete wavelet transform process. The two-dimensional inverse discrete wavelet transform process is executed in a sequence opposite to the forward discrete wavelet transform, but since its details are known to those who are skilled in the art, a description thereof will be omitted.

FIG. 12B shows the arrangement of the processor 902. The input transform coefficients undergo two filter processes of filters u and p, and are added after being up-sampled by up samplers 1201, thus outputting an image signal x'. These processes are described by:

$$x'(2n)=s'(n)-\text{floor}((d'(n-1)+d'(n))/4) \quad (13)$$

$$x'(2n+1)=d'(n)+\text{floor}((x'(2n)+x'(2n+2))/2) \quad (14)$$

Since the forward and inverse discrete wavelet transform processes given by equations (1), (2), (13), and (14) satisfy a perfect reconstruction condition, the restored image signal x' matches the original image signal x as long as the quantization step Δ is "1" and all bit planes are decoded in bit plane decoding in this embodiment.

With the aforementioned process, the original image is restored and is supplied to the image output unit 10. Note that the image output unit 10 may be an image display device such as a monitor or the like, or may be a storage device such as a magnetic disk or the like.

An image encoded by the spatial scalable scheme will be explained below.

The image display pattern upon restoring and displaying an image in the aforementioned sequence will be explained using FIGS. 13A and 13B.

Figure 13A:
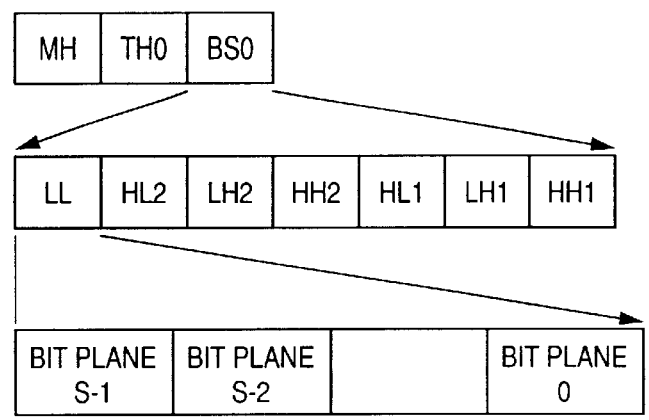
FIGS. 13A and 13B are views for explaining an example of a code sequence in case of spatial scalability, subbands upon decoding the code sequence, the sizes of images to be displayed in correspondence with the progress of decoding, and a change in reproduced image upon decoding code sequences of subbands.
Figure 13B:
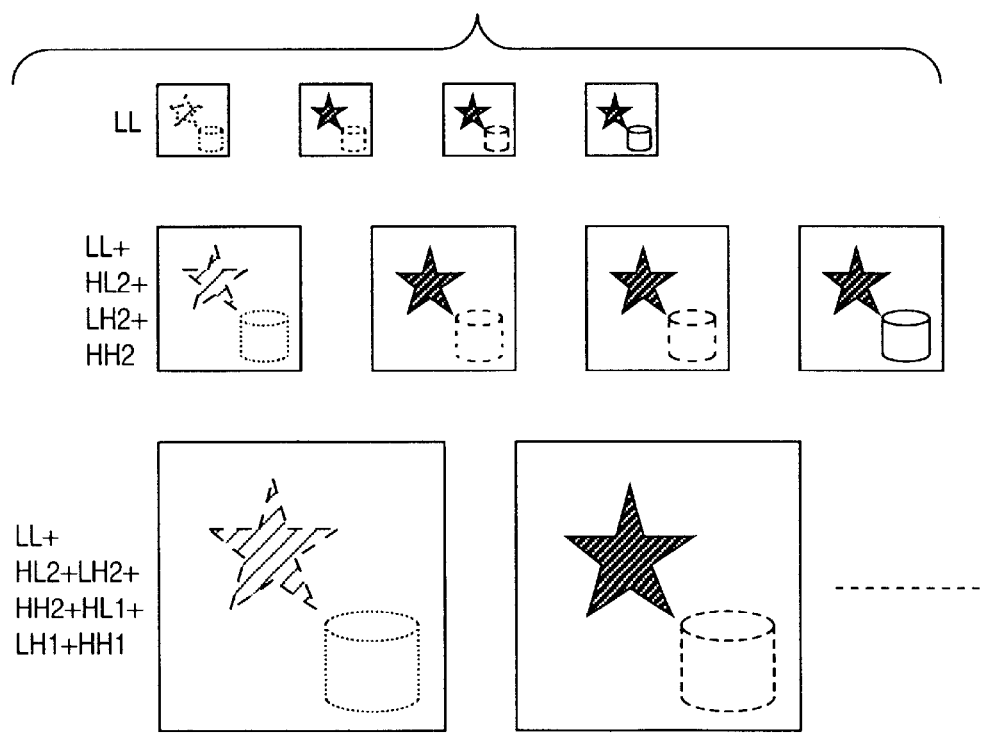

FIG. 13A shows an example of a code sequence, the basic format of which is based on FIGS. 8A to 8D. In this case, the entire image is set as one tile and, hence, the code sequence includes only one tile header (TH0) and bitstream (BS0). In this bitstream (BS0), codes are set in turn from LL as a subband corresponding to the lowest resolution to HH1 in ascending order of resolution. Furthermore, in each subband, codes are set from an upper bit plane (bit plane (S-1)) to a lower bit plane (bit plane 0).

The decoding apparatus sequentially reads this bitstream, and displays an image upon completion of decoding of codes of each bit plane. FIG. 13B shows the respective subbands, the sizes of images to be displayed in correspondence with the subbands, and changes in reproduced image upon decoding a code sequence of each subband. In FIG. 13B, a code sequence corresponding to LL is sequentially read out, and image quality gradually improves along with the progress of the decoding processes of the respective bit planes. At this time, the star-shaped portion used as the designated region upon encoding is restored with high image quality earlier than other portions.

This is because the quantizer 3 bit-shifts up the quantization indices which belong to the designated region upon encoding, and these quantization indices are decoded at earlier timings than other portions upon bit plane decoding. The same applies to other resolutions, i.e., the designated region portion is decoded with higher image quality.

Furthermore, upon completion of decoding of all the bit planes, the designated region portion and other portions have equal image quality. However, when decoding is interrupted in the middle of the decoding processes, in the present moment, an image with the designated region portion (star-shaped portion) restored to have higher image quality than other regions can be obtained.

Rasterization upon encoding by the SNR scalable scheme will be explained below.

The image display pattern upon restoring and displaying an image in the aforementioned sequence will be explained using FIGS. 14A and 14B.

Figure 14A:
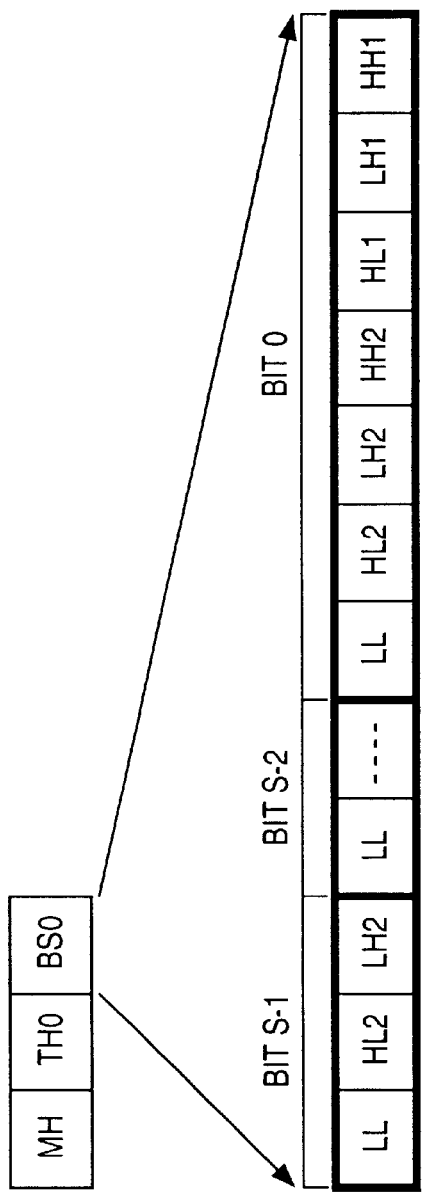
FIGS. 14A and 14B are views for explaining an example of a code sequence in case of SNR scalability and its decoding process.
Figure 14B:
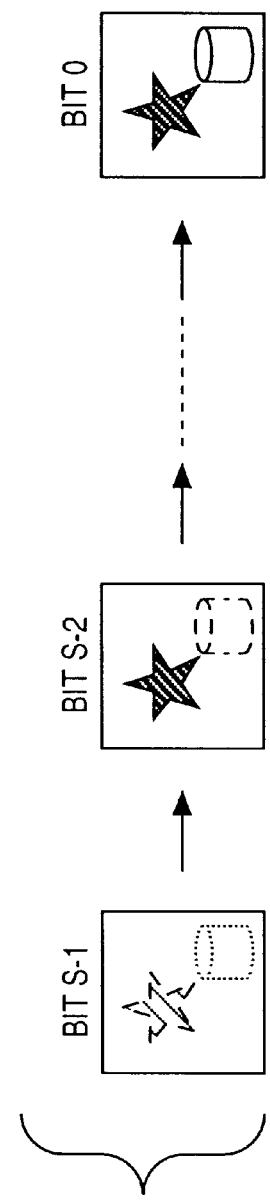

FIG. 14A shows an example of a code sequence, the basic format of which is based on FIGS. 9A to 9D, but the entire image is set as one tile in this case. Hence, the code sequence includes only one tile header (TH0) and bitstream (BS0). In this bitstream (BS0), codes are set from the most significant bit plane (bit S-1) to the least significant bit plane (bit 0).

The decoding apparatus sequentially reads this bitstream, and displays an image upon completion of decoding of codes of each bit plane. In FIG. 14B, as the decoding processes of the respective bit planes progress in the order of bit (S-1), bit (S-2), . . . , bit 0, the image quality gradually improves. In this case, the star-shaped portion used as the designated region upon encoding is restored with high image quality earlier than other portions.

This is because the quantizer 3 bit-shifts up the quantization indices which belong to the designated region upon encoding by the encoding apparatus, and these quantization indices are decoded at earlier timings than other portions upon bit plane decoding.

Furthermore, upon completion of decoding of all the bit planes, the designated region portion and other portions have equal image quality. However, when decoding is interrupted in the middle of the processes, in the present moment, an image with the designated region portion (star-shaped portion) restored to have higher image quality than other regions can be obtained.

In the aforementioned embodiment, when the entropy decoder 7 limits (ignores) lower bit planes to be decoded, an mount of the encoded data to be received or processed is reduced, and the compression ratio can be consequently controlled. In this manner, a decoded image with required image quality can be obtained from only encoded data of the required data volume. When the quantization step Δ upon encoding is "1", and all bit planes are decoded upon decoding, the restored image matches an original image, i.e., reversible encoding and decoding can be implemented.

Using the aforementioned function of limiting lower bit planes, since the code sequence to be decoded includes only bits corresponding to the designated region in larger quantity than other regions, the same effect as that upon decoding image data which is obtained by encoding only the designated region at a low compression ratio and as a high-quality image can be consequently obtained.

Coding using wavelets has been generally explained, but the coding is not limited to an encoding by using the wavelet transformation. This embodiment is characterized by detecting an irradiated region, and compressing (or reversibly compressing) a portion obtained by removing an X-ray through region from the irradiated region as a region of interest (designated region) with high quality.

Note that the scope of the present invention includes a case wherein quantization, dequantization, and the like are omitted from the encoding and decoding processes. In such case, in place of shifting up the quantization indices, bit planes obtained by shifting up values before quantization can be encoded.

Note that the present invention may be applied to either a system constituted by a plurality of devices (e.g., a host computer, an interface device, a reader, a printer, and the like), or an apparatus consisting of a single equipment (e.g., a copying machine, a facsimile apparatus, or the like).

The objects of the present invention are also achieved by supplying a storage medium (or recording medium), which records a program code of a software program that can implement the functions of the above-mentioned embodiments to the system or apparatus, and reading out and executing the program code stored in the storage medium by a computer (or a CPU or MPU) of the system or apparatus. In this case, the program code itself read out from the storage medium implements the functions of the above-mentioned embodiments, and the storage medium which stores the program code constitutes the present invention. The functions of the above-mentioned embodiments may be implemented not only by executing the readout program code by the computer but also by some or all of actual processing operations executed by an operating system (OS) running on the computer on the basis of an instruction of the program code.

Furthermore, the functions of the above-mentioned embodiments may be implemented by some or all of actual processing operations executed by a CPU or the like arranged in a function extension card or a function extension unit, which is inserted in or connected to the computer, after the program code read out from the storage medium is written in a memory of the extension card or unit.

As described above, according to this embodiment, since the through region of the irradiated region of an X-ray image is encoded at a high compression ratio or is removed from the region to be encoded, a high compression ratio can be realized as a whole while preserving high image quality of the region of interest of an X-ray diagnostic image.

The present invention is not limited to the above embodiments and various changes and modifications can be made within the spirit and scope of the present invention. Therefore, to apprise the public of the scope of the present invention, the following claims are made.

What is claimed is:

1. An image processing apparatus for encoding an X-ray image, comprising:
   an input unit configured to input the X-ray image;
   a region of interest designation unit configured to detect a through region in an X-ray irradiation field of the X-ray image input by said input unit, and to designate a region of interest in the X-ray irradiation field;
   a transformation unit configured to transform the X-ray image using a discrete wavelength transformation to obtain coefficient values of the X-ray image;
   an encoding unit configured to shift up bits representing coefficient values corresponding to the region of interest relative to bits representing coefficient values corresponding to a region of non-interest, among the coefficient values obtained by said transformation unit, and to encode the region of interest and the region of non-interest,
   wherein said encoding unit more preferentially encodes upper bits than lower bits in a predetermined unit area of the X-ray image and the shift up is performed in order to more preferentially encode the region of interest than the region of non-interest without substantially changing the content of the region of interest.

2. The image processing apparatus according to claim 1, wherein said region of interest designation unit detects the through region on the basis of a histogram of pixel values in the irradiation field.

3. The image processing apparatus according to claim 1, wherein said region of interest designation unit removes an isolated point and a remaining through region in the irradiation field other than the through region, and designates a continuous image region as the region of interest.

4. The image processing apparatus according to claim 1, wherein said region of interest designation unit determines the presence of an irradiation field stop when an average pixel value of a peripheral region of the X-ray image is a predetermined value or more smaller than an average pixel value of a central region of the X-ray image, and detects the irradiation field on the basis of second derivatives of profiles extracted in vertical and horizontal directions of the X-ray image.

5. The image processing apparatus according to claim 1, wherein said encoding unit performs entropy-encoding on the coefficient values.

6. The image processing apparatus according to claim 1, further comprising a quantizer unit configured to quantize the coefficient values corresponding to the region of interest after shifting up the coefficient values relative to coefficient values corresponding to the non-region-of-interest.

7. The image processing apparatus according to claim 1, further comprising:
   a decoder configured to decode a code sequence; and
   an inverse discrete wavelet transformer configured to transform coefficient values decoded by said decoder using an inverse discrete wavelet transformation.

8. An image processing method for encoding an X-ray image, comprising:
   inputting the X-ray image;
   a region of interest designation step of detecting a through region in an X-ray irradiation field of the X-ray image input in said inputting step, and designating a region of interest in the X-ray irradiation field;
   a transformation step of transforming the X-ray image using a discrete wavelength transformation to obtain coefficient values of the X-ray image;
   an encoding step of shifting up bits representing coefficient values corresponding to the region of interest relative to bits representing coefficient values corresponding to a region of non-interest, among the coefficient values obtained in said transformation step, and encoding the region of interest and the region of non-interest,
   wherein said encoding step more preferentially encodes upper bits than lower bits in a predetermined unit area of the X-ray image and the shifting up step is performed in order to more preferentially encode the region of interest than the region of non-interest without substantially changing the content of the region of interest.

9. The image processing method according to claim 8, wherein said region of interest designation step detects the through region on the basis of a histogram of pixel values in the X-ray irradiation field.

10. The image processing method according to claim 8, wherein said region of interest designation step removes an isolated point and a remaining through region in the irradiation field, other than the through region, and designates a continuous image region as the region of interest.

11. The image processing method according to claim 8, wherein said region of interest designation step determines the presence of an irradiation field stop when an average pixel value of a peripheral region of the X-ray image is a predetermined value or more smaller than an average pixel value of a central region of the X-ray image, and detects the irradiation field on the basis of second derivatives of profiles extracted in vertical and horizontal directions of the X-ray image.

12. The image processing method according to claim 8, wherein said encoding step performs entropy-encoding on the coefficient values.

13. The image processing method according to claim 8, further comprising a step of quantizing the coefficient values corresponding to the region of interest after shifting up the coefficient values relative to coefficient values corresponding to the non-region-of-interest.

14. The image processing method according to claim 8, further comprising:
   a decoding step of decoding a code sequence;
   a dequantization step of dequantizing coefficient values decoded in said decoding step; and
   an inverse discrete wavelet transform step of transforming the coefficient values dequantized in said dequantization step using an inverse discrete wavelet transformation.

15. A computer readable storage medium that stores a program for implementing an image processing method for encoding an X-ray image, the method comprising:

inputting the X-ray image;

a region of interest designation step of detecting a through region in an X-ray irradiation field of the X-ray image input in said inputting step, and designating a region of interest in the X-ray irradiation field;

a transformation step of transforming the X-ray image using a discrete wavelength transformation to obtain coefficient values of the X-ray image;

an encoding step of shifting up bits representing coefficient values corresponding to the region of interest relative to bits representing coefficient values corresponding to a region of non-interest, among the coefficient values obtained in said transformation step, and encoding the region of interest and the region of non-interest, wherein said encoding step more preferentially encodes upper bits than lower bits in a predetermined unit area of the X-ray image and the shifting up step is performed in order to more preferentially encode the region of interest than the region of non-interest without substantially changing the content of the region of interest.

16. The computer readable storage medium according to claim 15, wherein said region of interest designation step detects the through region on the basis of a histogram of pixel values in the Xray irradiation field.

17. The computer readable storage medium according to claim 15, wherein said region of interest designation step removes an isolated point and a remaining through region in the irradiation field other than the through region, and designates a continuous image region as the region of interest.

18. The computer readable storage medium according to claim 15, wherein said region of interest designation step determines the presence of an irradiation field stop when an average pixel value of a peripheral region of the X-ray image is a predetermined value or more smaller than an average pixel value of a central region of the X-ray image, and detects the irradiation field on the basis of second derivatives of profiles extracted in vertical and horizontal directions of the X-ray image.

19. The computer readable storage medium according to claim 15, wherein said encoding step entropy-encodes the coefficient values.

20. The computer readable storage medium according to claim 15, further comprising a quantization step for quantizing the coefficient values corresponding to the region of interest after shifting up the coefficient values relative to coefficient values corresponding to the non-region-of-interest.

21. The computer readable storage medium according to claim 15, further comprising:

a decoding step of decoding a code sequence;

a dequantization step of dequantizing coefficient values decoded in said decoding step; and an inverse discrete wavelet transform step of computing an inverse transform of the coefficient values dequantized in said dequantization step using inverse discrete wavelet transformation.

* * * * *

UNITED STATES PATENT AND TRADEMARK OFFICE
CERTIFICATE OF CORRECTION

PATENT NO.    : 6,766,044 B1
DATED         : July 20, 2004
INVENTOR(S)   : Osamu Tsujii It is certified that error appears in the above-identified patent and that said Letters Patent is hereby corrected as shown below:

Column 7,
Line 38, "stated," should read -- state, --.

Column 12,
Line 23, "mount" should read -- amount --.

Column 14,
Lines 5 and 58, "non-region-of-interest" should read -- region of non-interest --.

Column 15,
Line 27, "Xray" should read -- X-ray --.

Column 16,
Line 19, "non-region-of" should read -- region of non --.

Signed and Sealed this

Twenty-fifth Day of January, 2005

JON W. DUDAS
*Director of the United States Patent and Trademark Office*